US010463620B2

(12) United States Patent
Boghmans et al.

(10) Patent No.: US 10,463,620 B2
(45) Date of Patent: Nov. 5, 2019

(54) PROCESS FOR PREPARING A DIRECTLY COMPRESSIBLE ERYTHRITOL AND USES THEREOF

(71) Applicant: Cargill, Incorporated, Wayzata, MN (US)

(72) Inventors: Catherine Patricia L. Boghmans, Burst (BE); Petrus Wilhelmus Hubertus Antonius De Cock, Keerbergen (BE)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/518,371

(22) PCT Filed: Oct. 16, 2015

(86) PCT No.: PCT/US2015/055987
§ 371 (c)(1),
(2) Date: Apr. 11, 2017

(87) PCT Pub. No.: WO2016/061486
PCT Pub. Date: Apr. 21, 2016

(65) Prior Publication Data
US 2017/0304206 A1  Oct. 26, 2017

Related U.S. Application Data

(60) Provisional application No. 62/064,811, filed on Oct. 16, 2014.

(51) Int. Cl.
*A61K 9/16* (2006.01)
*A61K 47/26* (2006.01)
*A61K 9/20* (2006.01)

(52) U.S. Cl.
CPC .......... *A61K 9/1652* (2013.01); *A61K 9/1623* (2013.01); *A61K 9/1682* (2013.01); *A61K 9/205* (2013.01); *A61K 9/2018* (2013.01); *A61K 9/2095* (2013.01); *A61K 47/26* (2013.01)

(58) Field of Classification Search
CPC .. A61K 9/1652; A61K 9/2095; A61K 9/2018; A61K 9/1623; A61K 47/26
See application file for complete search history.

(56) References Cited

U.S. PATENT DOCUMENTS

| | | | |
|---|---|---|---|
| 5,202,507 A | 4/1993 | Ohshima et al. | |
| 5,973,212 A * | 10/1999 | De Sadeleer | A23G 1/56 426/548 |
| 6,165,511 A | 12/2000 | Schwarz et al. | |
| 6,274,727 B1 | 8/2001 | Maul et al. | |
| 6,287,596 B1 | 9/2001 | Murakami et al. | |
| 6,849,286 B1 | 2/2005 | Bayerkohler et al. | |
| 7,338,677 B2 | 3/2008 | Song et al. | |
| 7,378,118 B2 | 5/2008 | Song et al. | |
| 8,052,999 B2 | 11/2011 | Politi et al. | |
| 8,545,889 B2 | 10/2013 | Norman et al. | |
| 8,581,134 B2 | 11/2013 | Politi et al. | |
| 8,617,588 B2 | 12/2013 | Tillotson et al. | |
| 2004/0071772 A1 | 4/2004 | Narita et al. | |
| 2004/0121006 A1 | 6/2004 | Narita et al. | |
| 2007/0092562 A1 | 4/2007 | Norman et al. | |
| 2008/0146520 A1 | 6/2008 | Block et al. | |
| 2008/0299194 A1 | 12/2008 | Kolter et al. | |
| 2010/0074948 A1 | 3/2010 | Ramtoola et al. | |
| 2010/0178349 A1* | 7/2010 | Kolter | A61K 9/0056 424/489 |
| 2010/0203190 A1 | 8/2010 | Barkalow et al. | |
| 2010/0226964 A1 | 9/2010 | Tillotson et al. | |
| 2011/0089087 A1 | 4/2011 | Politi et al. | |
| 2012/0040001 A1 | 2/2012 | Koizumi et al. | |
| 2012/0149784 A1 | 6/2012 | Boghmans et al. | |
| 2012/0283338 A1 | 11/2012 | Adkins et al. | |
| 2013/0040018 A1 | 2/2013 | Alexandre et al. | |
| 2013/0216659 A1 | 8/2013 | Jensen et al. | |
| 2013/0216668 A1 | 8/2013 | Jensen et al. | |
| 2013/0216677 A1 | 8/2013 | Jensen et al. | |
| 2013/0274348 A1 | 10/2013 | Sato et al. | |
| 2014/0093574 A1 | 4/2014 | Tillotson et al. | |
| 2014/0199461 A1 | 7/2014 | De Baets | |
| 2014/0314845 A1 | 10/2014 | Yamanaka | |

FOREIGN PATENT DOCUMENTS

| | | |
|---|---|---|
| EP | 0511761 A1 | 11/1992 |
| EP | 0555980 A1 | 8/1993 |
| EP | 0922464 A1 | 6/1999 |
| EP | 1161940 B1 | 6/2005 |
| EP | 1757193 A2 | 2/2007 |
| EP | 1245582 B1 | 7/2007 |
| EP | 1524913 B1 | 9/2007 |
| EP | 1830662 A2 | 9/2007 |
| EP | 1944017 A2 | 7/2008 |
| EP | 2081669 A2 | 7/2009 |
| EP | 2091351 A2 | 8/2009 |
| EP | 2095812 A1 | 9/2009 |
| EP | 2142170 B1 | 11/2011 |
| EP | 1551232 B1 | 4/2012 |
| EP | 2503902 A1 | 10/2012 |
| EP | 1465604 B1 | 7/2013 |
| GB | 2391449 B | 5/2006 |
| JP | H04335870 A | 11/1992 |
| JP | 2003176242 A | 6/2003 |
| JP | 2006265242 A | 10/2006 |
| JP | 2007153887 A | 6/2007 |

(Continued)

OTHER PUBLICATIONS

Scott-Thomas, "Corn products introduces compressible erythritol for confectionary, tablets", Food Navigator-USA.com, Mar. 23, 2011.

*Primary Examiner* — Carlos A Azpuru

(57) ABSTRACT

A process for preparing a directly compressible erythritol composition is provided that is suitable for tableting. The composition includes a binding agent such as maltodextrin.

9 Claims, No Drawings

(56) References Cited

FOREIGN PATENT DOCUMENTS

| | | |
|---|---|---|
| JP | 2009520744 A | 5/2009 |
| JP | 2013502383 A | 1/2013 |
| WO | 2004089343 A1 | 10/2004 |
| WO | 2007055427 A1 | 5/2007 |
| WO | 2007071581 A2 | 6/2007 |
| WO | 2011020526 A1 | 2/2011 |
| WO | 2012029838 A1 | 3/2012 |

* cited by examiner

PROCESS FOR PREPARING A DIRECTLY COMPRESSIBLE ERYTHRITOL AND USES THEREOF

CROSS REFERENCE TO RELATED APPLICATIONS

This application is a section 371 national-stage phase of International Application No. PCT/US15/055987, filed 16 Oct. 2015 entitled PROCESS FOR PREPARING A DIRECTLY COMPRESSIBLE ERYTHRITOL AND USES THEREOF, which claims priority to U.S. Application Ser. No. 62/064,811, filed 16 Oct. 2014 entitled PROCESS FOR PREPARING A DIRECTLY COMPRESSIBLE ERYTHRITOL AND USES THEREOF, which are hereby incorporated by reference in their entirety.

BACKGROUND

Tablets are a commonly employed form to deliver ingredients, whether an active pharmaceutical ingredient (API), a flavoring, an aroma or a colorant. Tablets can be produced by compressing appropriately formulated excipients with the API or other desirable or required ingredients.

With an interest in sugar-free, low calorie or non-cariogenic products, the use of sugar alcohols in tablet applications is an attractive alternative. But some sugar alcohols for tablet applications, such as erythritol, have been a challenge because they do not compress as easily and if they do, the resulting product is much too brittle or too soft.

SUMMARY

Disclosed here is a process for the production of an erythritol-containing composition suitable for use as a directly compressible tableting composition. Aspects of the invention provide a process for preparing a compressible composition, the process comprising:
a) providing erythritol particles to be agglomerated into a fluid bed;
b) atomizing or spraying an agglomeration liquid on the solid particles;
c) agglomerating the erythritol with the agglomeration liquid; and
e) drying the agglomerated product to the desired moisture content.

In other aspects, the invention provides a directly compressible tableting composition, comprising an agglomerated product comprising:
(a) erythritol from about 80 to about 99 percent, based on the dry weight of the composition; and
(b) from about 1 to about 20 percent, based on the dry weight of the composition, of an agglomeration fluid, the agglomerated product being prepared in a fluid bed by the process which comprises:
a) providing erythritol particles to be agglomerated into a fluid bed;
b) atomizing or spraying an agglomeration liquid on the erythritol particles;
c) agglomerating the erythritol particles and agglomeration liquid; and
e) drying the agglomerated product.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention. All patents, published applications, other publications, and pending patent applications, if any, are incorporated herein by reference.

The term "agglomeration" is referred to as a process to achieve particle size enlargement of materials such as powders. The term granulation is used interchangeably with agglomeration.

The term "binder" when used in reference to the agglomeration product refers to a substance to help solid particles stick together or impart a desirable characteristic to the solid particles or both.

The term "excipient" when used in reference to tableting refers to substances, other than the API, to either aid the processing or manufacture, protection, support, or enhancement of stability, bioavailability or patient or consumer acceptability, to assist in the product identification, or to enhance any other attributes of the overall safety, effectiveness and sensorial acceptability of the tablet.

The term "tablet" as used herein, includes tablets in any form, shape and of any physical, chemical or sensory property, and tablets for any route of administration, indication and application. The term includes but is not limited to molded tablets, chewable tablets (e.g. chewy squares or gums), pellets, pills, triturates, hypodermic tablets, effervescent tablets, controlled-release tablets, and immediate release tablets (e.g., oral disintegrating or oral dispersible tablets).

Tablets are typically prepared as a solid body formed by placing powder, which contain excipients and depending on use, an active ingredient or other suitable ingredients. When sufficient pressure is applied to this powder mixture, the particles stick together and thereby form the solid body tablet. Such directly compressible tableting process is preferable in the tableting industry because of cost advantages. Not all ingredients, however, can be directly compressed into tablets. In such cases, the non-compressible ingredients (e.g. excipients or other ingredients) may be granulated or agglomerated to impart desired tableting characteristics such as flow/ability, particle size, surface area and the like.

The known granulation methods used are the wet method or the dry method. The wet method, as the name suggests, uses a liquid in the process, whereas the dry method does not. Wet granulation, which is most often used, involves many steps, including agglomerating (granulating) of dry primary powder particles (e.g. active ingredients and/or excipients) in the presence of a granulating or agglomerating fluid upon agitation using low-shear or high-shear mixers or fluidized beds, wet sieving (wet screening) to remove larger lumps, drying the granulation, and milling or sieving (screening) the dried granulation to achieve a granulation having the desired granule size distribution. The resultant granulation or agglomerated product may be subsequently tabletted.

As mentioned previously, erythritol, while attractive as a sugar-free alternative, does not possess the requisite attributes for use in a direct compression tableting processes.

Disclosed here is a process for the production of an erythritol-containing composition suitable for use as a directly compressible tableting composition. The erythritol-containing composition was prepared by agglomerating or granulating erythritol with a binder such as maltodextrin. To prepare the disclosed agglomerated product, a fluidized bed technique was used. The resulting agglomerate may be used for tableting by direct compression. Such directly compressible tablets produced with the disclosed agglomerated product are characterized by tablet tensile strength, compaction and hardness. In addition, the disclosed process provides several processing and cost advantages over the known granulation or spray drying methods. In the disclosed method, a smaller fraction of the agglomerating solution is required; hence the energy used to form and spray the solution is reduced. This in turn reduces drying energy and drying time thereby reducing production costs.

In the disclosed fluid bed agglomeration process, solid particles to be agglomerated are suspended in a continuous air stream and are sprayed with a solution (e.g. water or liquid binder) referred to as the agglomerating fluid or solution into the fluidized bed so as to cause intimate commingling of solution and solid particles. This commingling allows adhesion or coalescence of solid particles and liquid to form agglomerated particles. The agglomerating solution is typically applied as a spray (e.g. mist-like) or atomized. In some embodiments, the spray may be applied intermittently and the bed particles are dried between spraying while they are continuously maintained suspended and in a fluidized state. Intermittent spraying and drying continues until all the agglomerating solution has been sprayed onto the bed. In other embodiments, spraying may be continuous until all the agglomerating solution has been sprayed onto the solid particles followed by drying. In still other embodiments, the drying occurs during the spraying. The moisture content of the bed is thereafter reduced to final desired moisture content or the equilibrium moisture content and the agglomerated particles are removed from the bed.

Air can be used as the gas for atomizing or spraying the agglomerating solution ("atomizing air"), controlling the spray pattern ("spray pattern air"), and suspending and fluidizing the solid particles in the body of the fluidized flow. Other suitable gases may likewise be employed (e.g., nitrogen).

The air pressure of the atomizing or sprayed air and pattern air and the pumping rate of the liquid binder solution are set and controlled in accordance with the particular agglomerate being produced. Also controlled is the quantity of fluidizing air being drawn to fluidize the bed particles, and the heat exchangers to set the temperature of the air introduced into the fluid bed.

In some embodiments, the atomizing air pressure and the pattern air pressure can be in the range of about 1 Bar to about 10 Bar, or 1 Bar to 5 Bar; the atomizing air flow in the range of about 100 L/h to about 200 the pattern air flow in the range of about 10 L/h to about 40 L/h, and the liquid binder flow rate in the range of about 15 ml/min to about 40 ml/min or 20 ml/min to about 30 ml/min. The spray nozzle can have an opening of about 2 mm. However, as would be understood by a person skilled in the art, the air flow rates and liquid flow rates can be different than those stated herein depending on the size of the fluidized bed dryer. The use of larger fluidized dryers would be desirable, which would require suitably higher flow rates.

The temperature of the agglomerating solution fed to the atomizer or sprayer is at room temperature (e.g., 20-30° C.) and the temperature of the gas (e.g., air), used in the drying is from about 7° C. to about 100° C. In other embodiments, the gas temperature is about 40 to about 90° C. In other embodiment, the gas temperature is about 75 to about 90° C. The temperature of the agglomerated product leaving the drier can be held around 30-60° C. In other embodiments, the temperature of the agglomerated product leaving the drier can be 35-50° C.

The agglomerated compositions may be dried by any method known in the art. In one embodiment, the agglomerated product can be dried in the fluid bed.

A commercially available fluidized bed for making the agglomerated product can include an Aeromatic-Fielder STREA-1™ fluid bed available from GEA Pharma Systems.

Erythritol is a well-known tetritol, which is obtainable via microbial processes or fermentation, chemical processes, preferably other than just hydrogenation of carbohydrates. In some embodiments, fermentation is used for erythritol production. Any erythritol grade may be used. Suitable grades include fine, micronized, turbomilled or the like and combinations thereof. Suitable erythritol particle sizes introduced into the fluid bed before the agglomeration process and reported as volume mean diameter range from about 1 micron to about 350 microns. In other embodiments the volume mean diameter include ranges about 1 micron to about 100 microns, or about 5 microns to about 40 microns. In one embodiment, the erythritol is about 15-30 microns. In still other embodiments, the erythritol is below 40 microns. Volume mean diameter can be measured by laser light diffraction.

Binders that impart good binding and hardness properties for tableting are used. The binder can be added in dry or liquid form.

The binders include maltodextin, isomalt and polyvinylpyrrolindone or combinations thereof. In one embodiment, the binder used is a maltodextrin. Maltodextrin is enzymatically derived from starch and has D-glucose units connected in chains of variable length. The glucose units are primarily linked with $\alpha(1\rightarrow4)$ glycosidic bonds. Maltodextrin is typically composed of a mixture of chains that vary from three to seventeen glucose units long. Maltodextrins are classified by DE (dextrose equivalent) and have a DE between 3 to 20. The higher the DE value, the shorter the glucose chains, the higher the sweetness, the higher the solubility and the lower heat resistance Maltodextrins from waxy maize or non-waxy maize are desirable. Maltodextrins with low dextrose equivalents (DE) such as below 15 are desirable. In one embodiment, a waxy maize maltodextrin having a DE below 15 can be used.

The binder may be added to the erythritol in dry or liquid form. When adding binder in dry form, water is used as the agglomerating solution to be sprayed. In one embodiment, the water may be applied at room temperature. In other embodiments, the water may be applied from about 40-60° C.

When adding binder in dry form, the dry binder may contain 5 to 25% by weight on a dry weight basis of the total composition (viz., erythritol and binder). In other embodiments, the dry binder can be from about 10 to 20 wt %, or 12 to 15 wt % on a dry weight basis of the total composition (viz., erythritol and binder). In one embodiment, maltodextrin is used in dry from in the range from about 10-15 wt %.

In one embodiment, the agglomeration fluid is a maltodextrin solution. The starting maltodextin solution concentration can range from about 25 wt percent to about 60 wt percent. In other embodiments, the maltodextrin solution can be from 30 wt to about 50 wt percent. Maltodextrin solution may be prepared in water. Depending on the amount of binder desired in the final agglomerated product, the amount of starting agglomeration fluid can be adjusted accordingly.

After the fluid bed agglomeration, the erythritol and binder amounts in the final agglomerated product may each have a suitable weight percentage in the agglomerated product. In one embodiment, erythritol is about 80 to about 99 weight percent and the binder is about 1 to about 20 weight % on a dry weight basis of the total agglomerated product. In other embodiments, erythritol is about 85 to about 95 weight % and the binder is from about 5 to about 15 weight % of the agglomerated product. In one embodiment, the erythritol is about 90 wt % and the binder is about 10 wt % on a dry weight basis of the total agglomerated product. In other embodiments, the erythritol is about 85 wt % and the binder is about 15 wt % on a dry weight basis of the total agglomerated product The final agglomerated product has a volume mean diameter from 50 µm to 700 µm. In other embodiments, the volume mean diameter can be from 50 µm to 500 µm, 100 µm to 400 µm, or from 100 µm to 300 µm.

The moisture content of the final agglomerated product is below 2%. In other embodiments, the moisture content is below 1.5%, or below 1%. Moisture content may be measured by the Karl Fisher method described in the European Pharmacopoeia.

The final agglomerated product may be used to form a tablet by known directly compressible tableting processes. If required, other aids in tableting such as a lubricant may be used. Exemplary lubricants include magnesium stearate, calcium stearate, stearic acid, sucrose fatty acid esters, or talc and the like or combinations thereof. In addition, surface active agents such as sodium lauryl sulfate, propylene glycol, sodium dodecanesulfonate, sodium oleate sulfonate, and sodium laurate mixed with stearates and talc, sodium stearyl fumarate, sucrose fatty acid esters, and the like can be added if required.

The proportions of the agglomerated product with other ingredients such as an API when tableted are not critical, and will depend upon other variables such as the API type and the unit dose desired in the tablet. In general, however, the agglomerated product when used in direct compression for tableting can range from about 1 to 99.5 wt % of the formulation used.

Suitable tablet presses that may be used include a single-punch eccentric press or a rotary press, such as one accommodating multiple exchangeable turrets. One example of a single-punch eccentric press is the Korsch XP1. An example of a rotary press is the Fette 1200-i.

Suitable compressibility as expressed by tensile strength can be obtained for tablets produced by the disclosed agglomerated product. At a compression force of 20 kN, the tensile strength can be at least 2.7 N/mm². In other embodiments, at a compression force of 20 kN, the tensile strength can be at least at least 2.9 N/min², or at least 3.5 N/mm².

At a compression force of 10 kN, the tablets produced with the disclosed agglomerated product by direct compression can have a hardness of at least 70 N. In other embodiments, the hardness can be at least 90 N, or at least 120 N. The tablets can also have a surface of at least 1 cm² and a weight of 350 mg with a variation of 5% as specified by the European Pharmacopoeia.

Tablets produced with the disclosed agglomerated product can be used in food, feed and pharma applications, cosmetics, detergents, fertilizer or agrochemical products. The disclosed agglomerated product can be used in food products such as, animal feed, health food, dietetic products, and animal medicine. The disclosed agglomerated product can also be used with bath agent, in agrochemical products, with fertilizer, with plant granules, with plant seeds or seed grains, and any other product that may be ingested by humans and/or animals or any other product which can benefit from the improved properties of the disclosed agglomerated product. The disclosed agglomerated product can be used as carrier for additives based on enzymes or microorganisms, detergent tablets, vitamins, flavors, perfumes, acids, sweeteners or various active ingredients with medicinal or non-medicinal applications.

The invention will now be described with reference to the following non-limiting examples.

EXAMPLES

Fluidized Bed Agglomeration

An Aeromatic-Fielder STREA-1™ fluid agglomerator from GEA Pharma Systems was used. The following operational parameters were used:

| | |
|---|---|
| Inlet air temperature | 85° C. |
| Erythritol loaded at room temperature | 1000 g per 300 ml of liquid |
| Atomizing air pressure | 2 Bar |
| Agglomerating solution | 300 ml per 1000 g of erythritol |
| Pump delivery rate of agglomerating solution | 25 ml per minute |
| Spraying temperature | Room temperature |
| Temperature during spraying | 40-45° C. |
| Drying temperature after agglomeration fluid is completely added | 56° C. |

The tablets were manufactured using single punch tableting press XP-1 from Korsch (Germany) or a rotary press Fette-1200i (Fette, Germany), with 24 stations.

Tablets were made using compression forces varying from 5 kiloNewton (kN) to 301 N. Tablets produced were round and flat with a surface of 1 cm², diameter of 11.3 mm and a weight of 350 mg. The thus obtained tablets were further analyzed as shown below:

The tablets were characterized by their hardness, friability and disintegration time. For each compression force; 10 tablets for hardness, 19 tablets for friability and 6 tablets for disintegration time were analyzed and the mean values were calculated. The following measurement methods for evaluating granule and tablet properties were employed:

The granules were characterized by their volume mean diameter (VMD) and density (loose and bulk density).

Size distribution was determined according to the European Pharmacopoeia 8.0, Test method 2.9.31 Particle size analysis by laser light diffraction. The equipment used to perform the measurement was the Helos KF Rodos T4.1 from SympaTec GmbH (Germany).

Density was determined according to the European Pharmacopoeia 8.0, Test method 2.9.34 Bulk density and tapped density of powders, using the Stampf volumeter from Jel (Germany).

Hardness, e.g., the diametral crushing strength, was determined according to the European Pharmacopoeia 8.0 Test method 2.9.8 Resistance to crushing of tablets by using a conventional pharmaceutical hardness tester (hardness tester model Multicheck V, available from Erweka GmbH (Germany)). To compare values across different size tablets, the breaking strength was normalized for the area of the break. The normalized value, expressed as N/mm², is herein referred to as tensile strength (Ts) and calculated as follows:

$$Ts = 2H/\pi TD,$$

wherein H is the hardness, T the thickness and D the diameter of the tablet.

Friability measurements were determined according to the European Pharmacopoeia 8.0 Test method 2.9.7 Friability of uncoated tablets, using the PTF E from PharmaTest (Germany).

Disintegration time was determined according to the European Pharmacopoeia 8.0, Test method 2.9.1 Disintegration of tablets and capsules, using the ZT-73 from Erweka GmbH (Germany).

Example 1

Agglomeration with Use of Different Binders

Dry erythritol (Cargill Zerose™ erythritol finely milled) was agglomerated with different binders in dry form and with varying concentration ranges as shown in the table below. Agglomeration was carried out using a fluidized bed Aeromatic-Fielder Strea-I from GEA Pharma Systems. The fluid bed agglomerator was charged with 1000 g of a mixture of erythritol powder and dry binder at an inlet temperature of 85° C. Water at room temperature was used as the agglomerating solution and was delivered at a rate of 25 ml per minute until all the solution was completely added. The agglomerated product was dried in the fluid bed at a temperature of about 56° C. to a moisture content of less than 2 wt %.

99.5% of the obtained agglomerated product was blended with 0.5% of magnesium stearate (Parteck LubMST, from Merck in a powder blender (PharmaTech) at 27 rpm. A total of 300 g of powder blend was made. The agglomerated products were subsequently compressed in the XP-1 (Korsch) tableting equipment. If tablets were obtained, they were further evaluated for their tablet quality (hardness, friability, disintegration time).

TABLE 1

| Binder | Binder concentration used (%) | Compressible Product* |
|---|---|---|
| Glucose | 5-8-10 | --- to + |
| Maltitol (powder) | 5-10-15-20 | --- |
| Xanthan gum | 0.14 | --- |
| Gum acacia | 3.55 & 6.25 | --- |
| PVP | 5 & 7 | +++ |
| Sorbitol | 10-20-30 | + |
| Starch | 2 & 2.5 | --- |
| HPMC | 5 | --- |
| Isomalt | 20 | ++ |
| Maltodextrin | 8-10-15-20 | + to +++ |

*--- indicates that it was not possible to obtain a tablet at the evaluated compression forces
+ indicates a compressible tablet with a maximum hardness below 90N
++ indicates a compressible tablet with a maximum hardness of about 90 to 150N
+++ indicates a compressible tablet with a maximum hardness of about 150 to 200N.

Based on the compressibility of a tablet produced by direct compression, maltodextrin was found to be the best binder to use in combination with erythritol in fluid bed agglomeration.

Example 2

Agglomeration with Different Concentrations of Dry Maltodextrin Binder

Fine erythritol (Cargill Zerose™ erythritol finely milled) is agglomerated with different percentages of dry maltodextrin (Cargill C*Dry maltodextrin) as binder varying between 0% and 20% weight percent in a fluidized bed Aeromatic-Fielder Strea-I from GEA Pharma Systems. The fluid bed conditions and agglomeration conditions are as described above. Water at room temperature was used as the agglomerating solution and was delivered at a rate of 25 ml per minute until all the solution was completely added. The agglomerated product was dried in the fluid bed at a temperature of about 56° C. to a moisture content of less than 2 wt %.

Tablets were prepared and evaluated as described above and in Example 1.

TABLE 2

| Dry Binder | Binder Concentration (wt %) | Compressible Product |
|---|---|---|
| None | 0 | --- |
| maltodextrin | 5 | --- |
|  | 10 | ++ |
|  | 15 | +++ |
|  | 20 | +++ |

Based on the compressibility of a tablet produced by direct compression, dry maltodextrin at a concentration between 10-20 wt % was found to be a satisfactory binder concentration to use with erythritol.

Example 3

Maltodextrin Binder Under Different Processing Conditions

Dry erythritol (Cargill Zerose™ erythritol finely milled) was agglomerated with 15 wt % of maltodextrin (Cargill C*Dry maltodextrin) as binder in a fluidized bed using the Aeromatic-Fielder Strea-I from GEA Pharma Systems, but added under different conditions as described below:

Condition 1: dry maltodextrin, sprayed with water at room temperature;
Condition 2. dry maltodextrin, sprayed with water at a temperature from about 45° C. to about 60° C.); and
Condition 3. maltodextrin solution sprayed at room temperature.

Agglomeration was carried out as described above.
Tablets were prepared and evaluated as described above and in Example 1.

TABLE 3

| Conditions | Binder concentration used (%) | Compressible product |
|---|---|---|
| 1 | 15% | + |
| 2 |  | +++ |
| 3 |  | +++ |

Based on the compressibility of a tablet produced by direct compression, maltodextrin in solution form was found to be a satisfactory binder to use with erythritol.

Example 4

Varying Erythritol Particle Size

Erythritol (Cargill Zerose™ erythritol) with different volume mean diameters were used to prepare the agglomerated product. The different volume mean diameters were obtained via milling or sieving the erythritol crystals. The varying erythritol particle sizes were agglomerated with 15 wt % maltodextrin solution (Cargill C*Dry maltodextrin) as binder in a fluidized bed using the Aeromatic-Fielder Strea-I from GEA Pharma Systems and the conditions as described above.

Tablets were prepared and evaluated as described above and in Example 1.

TABLE 4

| Erythritol starting material particle size (μm) | Binder concentration (wt %) | Compressible product |
|---|---|---|
| 25 | 15% maltodextrin | +++ |
| 125 | | + |
| 250 | | --- |
| 500 | | --- |

Based on the compressibility of a tablet produced by direct compression, erythritol having a volume mean diameter of 25 μm resulted in the best agglomerated product being produced.

Example 5

Type of Maltodextrin Used

Erythritol (Cargill Zerose™ erythritol finely milled) is agglomerated with different types of maltodextrin as binder in dry form. The agglomerations were done in a fluidized bed Aeromatic-Fielder Strea-I from GEA Pharma Systems under conditions described above.

Water at room temperature was used as the agglomerating solution and was delivered at a rate of 25 ml per minute until all the solution was completely added. The agglomerated product was dried in the fluid bed at a temperature of about 56° C. to a moisture content of less than 2 wt %. Tablets were prepared and evaluated as described above and in Example 1.

TABLE 5

| Type of maltodextrin used | Binder Concentration (wt %) | Compressible Product |
|---|---|---|
| Non-waxy | 10 | + |
| Waxy | 10 | +++ |

Example 6

Tabletting Characteristics with 10 wt % Maltodextrin

Fine erythritol (Cargill Zerose™ erythritol 16969) was agglomerated with 10 wt % of maltodextrin (Cargill C*Dry MD 01955) solution as binder. The fluid bed conditions and agglomeration conditions are as described above. The maltodextrin solution was used as the agglomerating solution and was sprayed at room temperature and at a rate of 25 ml per minute until all the solution was completely added. The agglomerated product was dried in the fluid bed at a temperature of about 56° C. to a moisture content of less than 2 wt %.

Tablets were prepared and evaluated as described above
Hardness, tensile strength, friability and disintegration time were evaluated at two different compression forces.

TABLE 6

| Compression force (kN) | Hardness (N) | Tensile strength (N/mm$^2$) | Friability (%) | Disintegration time |
|---|---|---|---|---|
| 15.9 | 114 | 2.24 | 0.91 | 92 |
| 24.6 | 169 | 3.82 | 0.67 | 168 |

The invention claimed is:

1. An agglomerated product comprising:
   (a) erythritol from about 80 to about 99 percent, based on the dry weight of the composition; and
   (b) from about 1 to about 20 percent, based on the dry weight of the composition, of a waxy or non-waxy maize maltodextrin binder, the agglomerated product being prepared in a fluid bed by the process which comprises:
       a) providing erythritol particles to be agglomerated into a fluid bed;
       b) adding the maltodextrin binder to the erythritol particles;
       b) atomizing or spraying an agglomeration fluid comprising on the erythritol particles and maltodextrin binder;
       c) agglomerating the erythritol particles and maltodextrin binder; and
       e) drying the agglomerated product.

2. An agglomerated product comprising:
   (a) erythritol from about 80 to about 99 percent, based on the dry weight of the composition; and
   (b) from about 1 to about 20 percent, based on the dry weight of the composition, of an agglomeration fluid comprising a waxy or non-waxy maize maltodextrin binder solution, the agglomerated product being prepared in a fluid bed by the process which comprises:
       a) providing erythritol particles to be agglomerated into a fluid bed;
       b) atomizing or spraying the agglomeration fluid on the erythritol particles;
       c) agglomerating the erythritol particles; and
       e) drying the agglomerated product.

3. The composition of claim 2 wherein the erythritol particles have a volume mean diameter of 1 to about 350 microns.

4. The composition of any one of claim 2 wherein the erythritol particles have a volume mean diameter below 40 microns.

5. The composition of claim 2 wherein the agglomeration fluid is at room temperature.

6. The composition of claim 2 wherein the agglomeration fluid is at temperatures from 40-65° C.

7. The composition of claim 1 wherein the maltodextrin is from about 10-20 wt percent in the agglomerated product.

8. The composition of claim 2 wherein the agglomerated product is used for tableting by direct compression.

9. The composition of claim 8 wherein the tablet can be selected from the group consisting of molded tablets, chewable tablets, pellets, pills, triturates, hypodermic tablets, effervescent tablets, controlled-release tablets, and immediate release tablets.

* * * * *